United States Patent
Lenke et al.

(10) Patent No.: US 7,528,368 B2
(45) Date of Patent: May 5, 2009

(54) ELECTROSPRAY IONIZATION PROCESS AND ADD-ON DEVICE WITH SAMPLE INJECTION TIP

(75) Inventors: James H. Lenke, Morgantown, WV (US); Matthew Powell, Morgantown, WV (US)

(73) Assignee: Protea Biosciences, Inc., Morgantown, WV (US)

( * ) Notice: Subject to any disclaimer, the term of this patent is extended or adjusted under 35 U.S.C. 154(b) by 372 days.

(21) Appl. No.: 11/642,413

(22) Filed: Dec. 20, 2006

(65) Prior Publication Data

US 2007/0221861 A1    Sep. 27, 2007

Related U.S. Application Data

(63) Continuation-in-part of application No. 11/388,193, filed on Mar. 23, 2006, now abandoned.

(51) Int. Cl.
*H01J 49/10* (2006.01)
(52) U.S. Cl. .................. 250/288; 250/423 R
(58) Field of Classification Search .............. 250/288, 250/423 R
See application file for complete search history.

(56) References Cited

U.S. PATENT DOCUMENTS

| | | | |
|---|---|---|---|
| 4,160,161 A | 7/1979 | Horton | |
| 4,861,988 A | 8/1989 | Henion et al. | |
| 5,635,045 A | 6/1997 | Alam | |
| 5,668,370 A * | 9/1997 | Yano et al. | 250/288 |
| 5,840,169 A | 11/1998 | Andersen | |
| 5,858,195 A | 1/1999 | Ramsey | |
| 5,917,184 A * | 6/1999 | Carson et al. | 250/288 |
| 6,462,337 B1 | 10/2002 | Li et al. | |
| 6,481,648 B1 | 11/2002 | Li et al. | |
| 6,737,640 B2 | 5/2004 | Kato | |
| 6,800,202 B2 | 10/2004 | Moon et al. | |
| 7,060,975 B2 | 6/2006 | Seaward et al. | |
| 7,098,451 B2 * | 8/2006 | Park | 250/288 |
| 2005/0145787 A1 * | 7/2005 | Prosser et al. | 250/288 |

FOREIGN PATENT DOCUMENTS

WO    WO2004017040 A2    2/2004

* cited by examiner

*Primary Examiner*—Kiet T Nguyen
(74) *Attorney, Agent, or Firm*—Spilman Thomas & Battle PLLC (57) ABSTRACT

A process for ionizing a liquid can comprising flowing the liquid through a capillary wire bonding tip and applying sufficient voltage to electrospray the liquid sample as it exits therefrom. The electrospray ionization process can further involve passing a liquid sample through an axially disposed aperture in a ceramic capillary wire bonding tip in which the terminus of the aperture flares into a bell-shape where the liquid sample exits therefrom. An add-on device can include gel electroelution and separating devices, and a ceramic capillary sample injection tip for carrying out the aforesaid electrospray ionization process. An adjustably mounted cartridge can also be provided with the add-on device for interchangeably receiving the ceramic capillary sample injection tip.

43 Claims, 8 Drawing Sheets

PRIOR ART

ELECTROSPRAY IONIZATION PROCESS AND ADD-ON DEVICE WITH SAMPLE INJECTION TIP

RELATED APPLICATIONS

This application is a continuation-in-part of U.S. patent application Ser. No. 11/388,193, filed Mar. 23, 2006 now abandoned.

BACKGROUND

The electrospray ionization process and add-on device with sample injection tip relate generally to electrospray ionization (ESI) processes and an add-device having an ESI sample injection tip and additional components for performing various sample preparation processes, such as, for example, gel electroelution and sample filtering/separating. More particularly, the electrospray ionization process relates to an electrospray ionization process having as much as 50 percent improvement in signal, and the add-on device can have a sample injection tip for such ESI process. Complimentary sample preparation devices can also be provided including a gel electroelution device and a separator device with tangential fluid flow.

Basically, "electrospray" is a method of generating a very fine liquid aerosol through electrostatic charging. In electrospray, a liquid is passed through a nozzle, and an electric potential is applied to the liquid either externally through conductive fittings or internally in-line with the solution flow path. There exists an air gap between the nozzle and the electrical ground whose resistance is large, and thus requires a large electrical potential relative to ground. When the applied voltage is of sufficient magnitude, the liquid solution can be induced to bridge the air gap and complete the electrical circuit. Essentially, as the applied voltage is increased, charge density builds at the tip of the nozzle and increases proportionally to the potential until the point at which the electric potential pull on the ions is greater than the reverse force of surface tension on the drop. As the charge density increases, fine droplets of liquid break away from the nozzle tip and form fine aerosol droplets (referred to as the plume) that transit the air gap to the electrical ground. During transit, the fine aerosol droplets are dried via passive and/or active evaporation, resulting in decreased droplet size and a consequent increase in charge density within the droplets. After a continued reduction in overall size, the increased Coulombic repulsions within the diminishing droplets lead to ejection of ions into the gas phase.

When used as a soft ionization method for chemical analysis, it is commonly called "electrospray ionization," or ESI. Here, ionization is the process of generating a gas phase ion from a liquid (typically) or solid chemical species. In this context, the method is characterized as "soft" because the chemical species are ionized by manipulating the solvent properties (i.e. pH), and not through collisional processes, as in "hard" ionization. Ionization is a critical event in mass spectrometry because the instrument functionally determines a molecule's mass-to-charge ratio, which requires that the molecule has a charge to be analyzed.

Electrospray ionization processes are well known in the art. A review of the historical development of electrospray ionization can be found in U.S. Pat. No. 6,462,337, by Li, et al. Electrospray ionization is commonly utilized in the analysis of biological samples, such as proteins and peptides that are susceptible to thermal degradation. Ionization of sample molecules can be controlled by adjusting the pH of the solvent to manipulate protonation and deprotonation events.

In mass spectrometric analysis, the basis for ESI is the establishment of an electrical circuit between the mass spectrometer and an electrode from the mass spectrometer in the flow path of the sample solution. A small air gap bridges the distance between the sample injection tip (i.e. tip emitter) and the mass spectrometer. When a voltage (1 to 5 kV) is applied to the liquid sample flowing through the ESI tip, a region of high charge density is produced at the outlet of the tip emitter. The electrospray process occurs at the outlet of the tip emitter. As the liquid begins to exit the tip emitter, it charges up and assumes a conical shape, referred to as a Taylor cone, so named after G. I. Taylor who described the phenomena in 1964. In general, the Taylor cone is formed due to the competing forces of the static electric field and the liquid's surface tension. The liquid assumes a conical shape because the force of the electric field can be felt at the apex of the cone as an extension of Newton's first law, which is commonly known as "the path of least resistance". Thus, the liquid, which is malleable, will transform to react to the potential to the extent that the force of the surface tension supplies an equal resistance. Therefore, at the tip of the Taylor cone, the liquid changes shape into a fine jet. However, this jet becomes unstable, and breaks up into a mist of fine, highly charged droplets, called the "plume." Desolvation of the droplets in the plume, combined with coulombic repulsion, leads to the production of gas phase ions. The continuity of the electrical circuit is completed as the ions transit the air space to the mass spectrometer. As soon as the ions enter the mass spectrometer, they are directed to the ion trap by ion optics for subsequent detection and determination of their mass-to-charge ratio. Thus, the ESI process is initiated by creating a Taylor cone of the fluid sample at the terminus of the aperture/sample injection tip, which can be referred to interchangeably as an "ESI tip," "ESI tip emitter," "tip emitter," or simply "emitter."

A conventional electrospray device for mass spectrometry can comprise, for example, an ESI tip in fluid communication with a sample liquid to be analyzed, and associated with a high voltage power supply. The ESI tip is positioned so as to emit the ionized liquid sample into a mass spectrometer. The ESI tip can be, for example, a hollow metal tube, e.g., a syringe needle. The liquid sample is passed through the tip, for example hydrodynamically, and the high-voltage power supply can be connected to the outside of the ESI tip, especially if the tip is electrically conductive or has a conductive coating. If the ESI tip is made from a non-conductive material, and the outside was not coated with a conductive material, the voltage could be applied to the liquid. The ESI tip is positioned in front of a plate, called a counter-electrode, which is commonly held at ground potential. When the power supply is turned on and adjusted for the proper voltage, the liquid sample flowing through the ESI tip transforms into the aforesaid Taylor cone as it is emitted from the ESI tip, and then ultimately ionizes into a fine continuous mist of highly charged droplets that transit the air space toward the counter-electrode.

Many different types of ESI tips are known in the art for use in combination with a mass spectrometer. All known conventional ESI tips are designed to have the "sharpest" tip possible. Conventional tip emitters can have an aperture diameter (ID) of around 25 µm or less, and an outer diameter (OD) as small as possible, i.e., the tip is made as "sharp" as possible. An example of a recently developed commercially available ESI tip is a fused silica capillary tip. This tip is formed by a process in which the capillary is heated and "pulled" to a fine pointed tip. Devices such as the Sutton Instrument laser puller can use laser light to heat the fused silica capillary while providing a pulling tension that draws the capillary into a much smaller diameter. When the stress point at the constriction becomes too great for the capillary, the constriction breaks into two sharp, i.e., finely pointed, tips. New Objective, Inc., of Woburn, Mass. produces fused silica capillary ESI tips in this fashion. Conductive coatings, such as gold, silver and polyaniline, can be placed on these ESI tips to permit direct connection of the electrode to the tip's exterior surface. Conventional stainless steel tip emitters are also commercially available from vendors such as from New Objective and Thermo Finnigan, Ltd., Hertfordshire, UK. Small hollow stainless steel tubes can either be fabricated with a small constant inner diameter, or drawn down to fine tip points on one end. These tips are naturally conductive, and the electrospray voltage can be directly applied to the outer surface of the tip. Advion Biosciences, Ithaca, N.Y., has also developed a silicon tip emitter for "static" ESI mass spectrometry. In a static ESI process, fluid flow through the column is not controlled by hydrodynamic pumping. Instead, a small amount of sample solution is injected into an inlet end of the tip, and capillary action draws the sample solution towards the outlet end of the tip at very low flow rates.

All "ESI tips" must create a Taylor cone in order to properly introduce the sample ions into the gas phase, where they can be steered by the electrical ion optics controlled within the mass spectrometer. Without this charge, the ions would pass straight to the vacuum waste and not be detected. Essentially, surface tension prevents the very tiniest drops of liquid from breaking free. If the drops are too large, the excess solvent causes formation of hydrates and other adjuncts, which interferes both with electrical steering of the ions in the ion optics and with accurate determination of the ion's mass-to-charge ratio, as the instrument will detect the combined mass of the complexes To overcome surface tension, organic solvent can be added. To break free, a high electric field (e.g., 2,000 V) can be applied to the liquid/tip, with the mass spectrometer being grounded. The high voltage is what breaks the micro droplets free from the bulk liquid. One way to concentrate the electric field ($V/cm^2$) without increasing the voltage is to minimize the area. This method is likely the reason that all (known) prior art, and current literature, teaches shrinking the ESI tip diameter to as small/sharp a point as possible.

Heretofore, it has been atypical to combine mass spectrometer sample preparation and sample injection in a single system or device. In part this is attributable to the very different scientific traditions of sample preparation (generally wet chemistry of some kind) versus the traditional biophysics of mass spectrometer sample injection and analysis. However, the prior art combination of sample preparation and injection is not unknown. For example, U.S. Pat. No. 6,942,793 discloses a liquid chromatography mass spectrometer in which a number of devices are combined in a single system. Known systems can include a pump, sample injector, plurality of separation columns including a first separation column and a second separation column, and a mass spectrometer. Such systems can also include a plurality of trap columns for retaining a sample component separated by the first separation column and a first switching valve for switching among one of the plurality of trap columns and another one of the plurality of trap columns at regular time intervals in such a way that when one of the plurality of trap columns is connected to the first separation column, another one of the plurality of trap columns is connected to the pump, and vice versa. A second switching valve can be employed to enable a trap column that is connected to the pump to be further connected to the second separation column, with the second separation column being connected to the mass spectrometer and capable of separating the sample component in a shorter time than the first separation column. Overall, U.S. Pat. No. 6,942,793 identifies the general benefits of combining sample preparation and injection in an overall coordinated system—a system to which the present invention nonetheless provides significant additional advantages as explained herein.

Continued challenges in sample preparation for mass spectrometry injection have to do with either or both of sample composition and/or contamination. For example, contamination in samples of interest is a serious problem in mass spectrometry. Mass spectrometry samples are so small that, literally, the wave of an ungloved hand near an exposed sample, or sample precursor, can deposit, sight unseen, enough keratin or other proteins from shed skin to skew the composition significantly. Also, preparation of mass spectrometry samples of biological materials usually requires the removal of abundant proteins, such as the ubiquitous albumin, to enrich the relative concentrations of the peptides or proteins of interest, and such preparation in turn needs to be conducted in a way that is both fast and efficient. Interchangeability is an issue, too. Just as in past decades users had to schedule and share their use of mainframe computers, today, mass spectrometry personnel need easy, efficient and contamination-free ways to share a single (very expensive) mass spectrometer.

Known ESI processes have heretofore enabled significant advances in the art, however, an ESI process as described herein can provide as much as about 50 percent improvement in signal over conventional ESI process. It would also be desirable to provide an add-on device that can implement such an ESI process and that can further provide an integrated approach to mass spectrometry that enables both optimal sample preparation and avoidance of contamination, while at the same time making the mass spectrometer available to as many users as possible.

SUMMARY

An electrospray ionization process for fluid samples is described, which in certain embodiments, can be utilized for mass spectrometry analysis of a fluid sample. An embodiment of an electrospray ionization process for mass spectrometry analysis can comprise flowing a liquid through a capillary wire bonding tip and applying sufficient voltage to initiate electrospray of the liquid as it is emitted from the capillary wire bonding tip into the mass spectrometer. Similarly, and perhaps more generally, the electrospray ionization process can comprise passing a liquid sample through an axially disposed aperture (e.g., a "capillary") in any "sample injection tip" wherein the aperture through the tip has a diameter of from about 5 µm to about 178 µm, and the terminus of the tip has an outer diameter of from about 25 µm to about 360 µm. In further embodiments, the sample injection tip can have one or more of the following structural features: the aperture can terminate in a "bell-shape" where the liquid is emitted; a chamfer can be provided where the aperture terminates at the face of the sample injection tip; and the chamfer diameter can be from about 5 µm to about 254 µm. In further embodiments, the chamfer diameter can be from about 38 µm to about 68 µm, and the outer diameter of the terminus can be from about 74 µm to about 200 µm. In still further embodiments: the aperture diameter can be about 34±5 µm (or from about 29 µm to about 39 µm); the chamfer (bell) diameter can be about 55±5 µm (or from about 50 µm to about 55 µm); and the outer diameter of the terminus can be about 135±5 µm (or from about 129 µm to about 140 µm).

The sample injection tip can be made from a ceramic material, such as a ceramic selected from the group of aluminum oxides, and can further can be selected from the group consisting of synthetic ruby (alumina doped with chromium oxide), and alumina doped with zirconia.

An add-on device with ESI sample injection tip is also described that can cooperate with a mass spectrometer to realize unique approaches to sample preparation, sample injection, and interchangeability among samples and users. The add-on device can generally comprise an ESI sample injection tip (which can be such as the capillary wire bonding tip described above in regard to the ESI process) and one or more sample preparation devices. The sample injection tip can further be mounted to the add-on device using a sample injection tip cartridge, such that the sample injection tip can be supported by the removable cartridge. Additionally, the sample injection tip cartridge can be mounted to the add-on device in a manner that permits the cartridge, and thus the sample injection tip, to rotate in at least one plane in order to adjust the angle at which the liquid sample is discharged from the sample injection tip, such as into a mass spectrometer. Additional associated sample preparation devices can comprise, for example, a gel electroelution device, and a separator device, which can each be provided in selective fluid communication with the sample injection tip. In this manner, a continuous sample preparation process culminating in injection of the processed sample into a mass spectrometer can be carried out efficiently while protecting the sample as much as possible from contamination during the process.

The gel electroelution device can generally comprise a gel spot cutter/column and a gel well within the gel spot column, wherein the gel well is adapted to receive a gel spot which occupies the entire cross-section of the gel spot column. In this manner, there will be no gap between the gel spot and gel spot column walls, so that admixing of fluid on either side of the gel spot can be prevented. The gel electroelution device can further comprise an inlet and an outlet, each in selective fluid communication with the gel spot column, a frit plug intermediate the gel spot well and the outlet; a positive electrode in fluid communication with said inlet, and a negative electrode in fluid communication with the outlet, such that an electric field is created in the same direction as the fluid flow. A purge line can also be provided in selective fluid communication with the gel spot column intermediate the gel well and the outlet.

The separator device, for example an in-line protein filter having a molecular weight cut-off filter (MWCO), can generally comprise a central well, an inlet port, filtrate port, and retentate port, each of which can be in selectively controlled fluid communication with the central well. A filter, such as the MWCO filter, can be provided intermediate the inlet and filtrate ports. The central well can be generally cylindrical, and each of the inlet port and retentate port can intersect the central well in a generally tangential orientation such that a cyclonic flow can be induced in the central well.

Additional sample preparation devices can include a chromatography capillary column ("nano") can be located adjacent the sample injection tip, and a high voltage source can be provided for applying a voltage to the sample fluid as required for the ESI process, to create a Taylor cone to properly electrospray the fluid sample. The sample injection tip can be fed from a sample source, which can also be in fluid communication with the other sample preparation components, and the fluid communication there between can be governed by one or more switching valves and associated electronics, such as a control panel, for example, an LCD touch screen, all of which can be governed by a computer, such as a personal computer.

Other details, objects, and advantages of the electrospray ionization process and add-on device with sample injection tip will become apparent from the following detailed description and the accompanying drawings figures of certain embodiments thereof.

BRIEF DESCRIPTION OF THE DRAWING(S)

A more complete understanding of the electrospray ionization process and add-on device with sample injection tip can be obtained by considering the following detailed description in conjunction with the accompanying drawings, in which:

FIG. 1b is a perspective view along lines 1b-1b of FIG. 1a;

FIGS. 2a, 2b, 2c and 2d are side sectional views of four alternate configurations of the capillary wire bonding tip shown in FIG. 1a;

FIG. 3 is a close up sectional view of the terminus of the capillary wire bonding tip shown in FIG. 1a;

FIGS. 7b and 7c are horizontal and vertical sectional views of the separator device shown in FIG. 7a.

DESCRIPTION OF CERTAIN EMBODIMENTS

Referring now to the drawing figures, wherein like reference numbers refer to like members, an electrospray ionization process for fluid samples is described which, in one embodiment, can be utilized for mass spectrometry analysis of a fluid sample. An embodiment of an electrospray ionization process can basically comprise flowing liquid through a capillary wire bonding tip and applying sufficient voltage to properly electrospray the liquid as it exits the capillary wire bonding tip. Similarly, and so as not to exclude any other similarly shaped tips which might be used as a sample injection tip, which tips may be constructed similarly to a capillary wire bonding tip but which may not be considered a "capillary wire bonding tip" per se, the electrospray ionization process can perhaps more generally comprise passing a liquid sample through an axially disposed aperture (e.g., a "capillary") in any type of sample injection tip wherein the aperture can have a diameter of from about 5 μm to about 178 μm, and the terminus of the tip can have an outer diameter of from about 25 μm to about 360 μm. Presently, capillary wire bonding tips are not commercially available with apertures less than about 25 μm, but it is anticipated that apertures down to about 5 μm will eventually be available. In further embodiments, the sample injection tip can have one or more of the following structural features: the aperture can terminate in a "bell-shape;" a chamfer can be provided where aperture terminates at the face of the sample injection tip; and the chamfer diameter (or "bell diameter") can be from about 5 μm to about 254

μm. In further embodiments, the chamfer diameter can be from about 38 μm to about 68 μm and the outer diameter of the terminus can be from about 74 μm to about 200 μm. In still further embodiments: the aperture diameter can be about 34±5 μm (or from about 29 μm to about 39 μm); the chamfer (bell) diameter can be about 55±5 μm (or from about 50 μm to about 55 μm); and the outer diameter of the terminus can be about 135±5 μm (or from about 129 μm to about 140 μm).

The capillary wire bonding tip, or a similarly constructed sample injection tip, can be made from a ceramic selected from the group of aluminum oxides, and can further can be selected from the group consisting of synthetic ruby (alumina doped with chromium oxide), and alumina doped with zirconia.

In the field of integrated circuit (PC chip) fabrication, ceramic capillary wire, or "ball," bonding tips are well known, as are the capillary wire/ball bonding processes for which such tips are designed to be used. Ceramic capillary tips are commercially available from a number of manufacturers, including the Small Precision Tools, Inc., and Gaiser Tool Company, of Ventura, Calif. In fact, Gaiser Tool's website states that they invented the ceramic capillary tip in 1970. Some examples of ceramic capillary wire bonding tips are described in, for example, U.S. Pat. Nos. 5,421,503, and 5,662,261 and 6,715,658.

The ceramic capillary wire bonding tip is a generally cylindrical article with a conical tip and an aperture, or "capillary hole," through the cylinder. In general, as described on the Gaiser Tool Co. website (www.gaisertool.com), the capillary hole can have a diameter as small as around 0.0010 inch, or 25 μm (microns).

Prior to the discovery by the inventors that the ceramic capillary wire bonding tip could in fact be utilized to produce an electrospray ionization of a fluid sample, i.e., could function as an ESI tip, no one had ever disclosed or suggested the possibility of such use of the ceramic capillary wire/ball bonding tip.

The ceramic capillary wire/ball bonding process is very different from an electrospray ionization process. The capillary wire/ball bonding process is basically a "welding" process in which a fine diameter metal wire, e.g., gold wire, is welded to/between electrical contacts to complete the external world connection to an integrated circuit, e.g., a PC chip. For a ceramic capillary wire bonding tip having a 25 μm (0.0010 in.) diameter capillary hole, a 20 μm (0.0008 in.) diameter wire is fed through the capillary during the welding process. As described on the Gaiser Tool Co. website (gaisertool.com), a capillary wire/ball bonding process can involve attaching, i.e., welding, a gold wire between a number of contacts in a procedure similar to "stitching" (or sewing).

In contrast, the ESI process, as described previously, involves flowing a liquid sample through the capillary and then applying a high voltage to the liquid sample until a Taylor cone is created, resulting in the ionization of the liquid sample. In mass spectrometry analysis, the ionized liquid sample is discharged into a mass spectrometer for analysis of the sample.

The prior art capillary wire/ball bonding tip structure is also distinct from conventional ESI tip emitters, in that conventional ESI tip emitters are typically designed to have as "sharp" a point at the terminus as possible, whereas the ceramic wire/ball bonding capillary has a comparatively "blunt" (flat) nose. In fact, the prior art teaching with respect to ESI tips is that an ESI tip should terminate in as fine a point as possible, as evidenced by the prior art fused silica capillary ESI tip emitter described previously. One possible explanation is that the conventional teaching is that, and without any intention of being bound by this belief, the reason prior art ESI tip emitters are sharply pointed is to try to increase the electric field by maintaining the same voltage and decreasing the outer diameter of the tip to as small a point as possible. This reasoning has the combined effect of putting more force (electric potential) in a smaller area to overcome the strong force of the surface tension. There is no known disclosure or teaching, apart from this application, that a capillary wire bonding tip could be used as an ESI tip.

However, not withstanding these differences and the conventional teaching, the ceramic capillary wire bonding tip displays unexpected and far superior results to conventional ESI tip emitters. Despite the blunt nose, the ceramic capillary wire bonding tip easily achieves the necessary high voltages/electric fields required for an ESI tip. In fact, the ionization process utilizing a ceramic capillary markedly improves mass spectral quality through a reduction of background noise in the spectra, with an average improvement of around fifty percent over electrospray ionization processes which employ a conventional ESI tip emitter.

Add-On Device

An add-on device is described which can cooperate with a mass spectrometer to realize unique approaches to sample preparation, sample injection, and interchangeability among samples and users. The add-on device can comprise the aforesaid ceramic capillary wire bonding tip as the sample injection tip. The sample injection tip can be fed from a sample source that can optimally be treated by one or multiple sample preparation components as can be governed by one or more switching valves and associated electronics including an optical touch screen, such as an LCD touch screen.

Additional sample preparation components can include an optional gel electroelution device which provides unique sample separation; and an optional separator device that can utilize tangential fluid flow. The gel electroelution device and separator device can operate in combination, or alone, and with or without chromatography columns or other separators. In this manner, a continuous sample preparation process culminating in injection of the processed sample into a mass spectrometer can be carried out efficiently while protecting the sample as much as possible from contamination during the process.

Figure 1A:
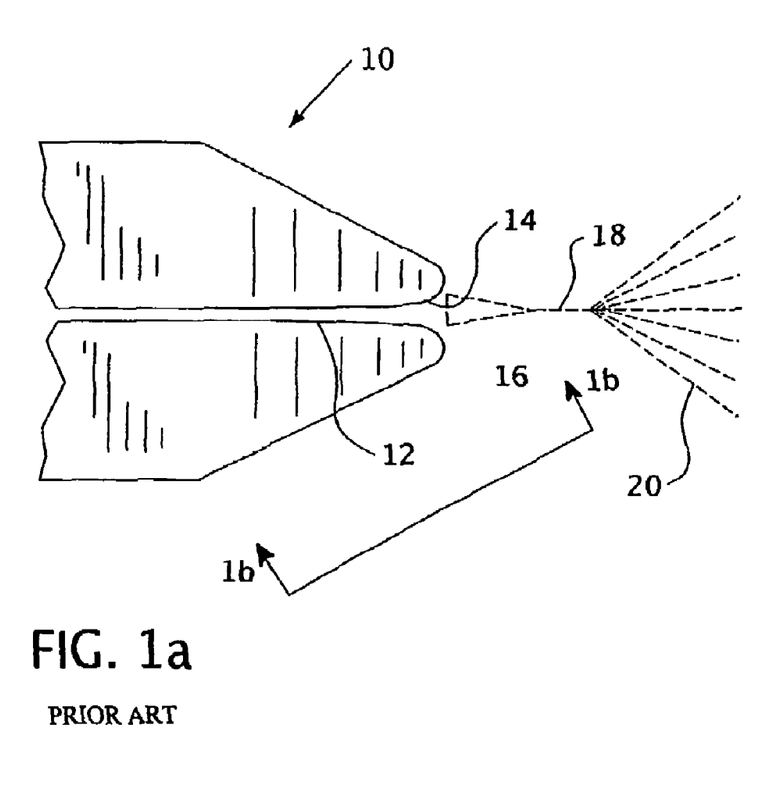
FIG. 1a is a side sectional view of a prior art capillary wire bonding tip.
Figure 1B:
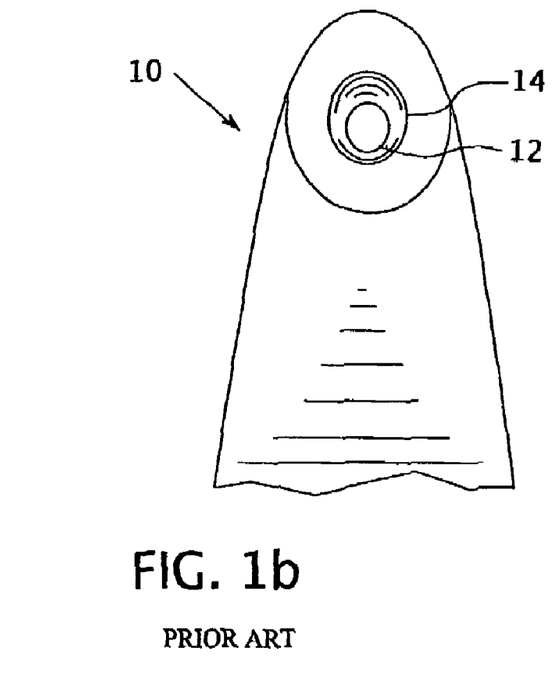
Figure 2A:
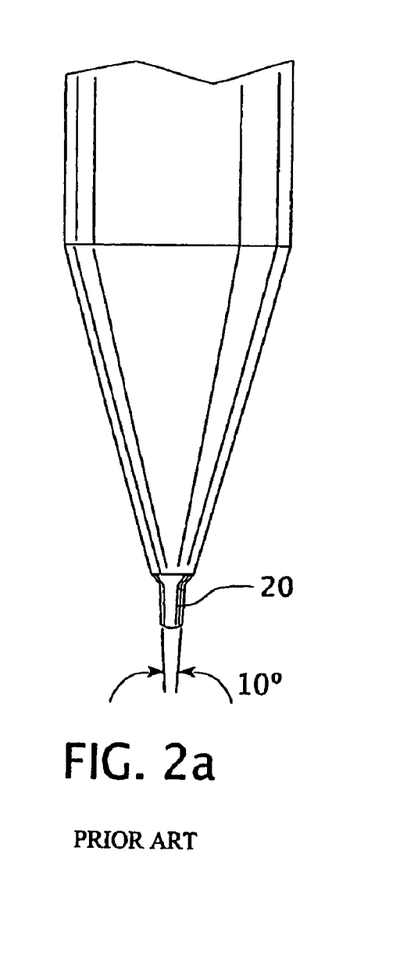
Figure 2B:
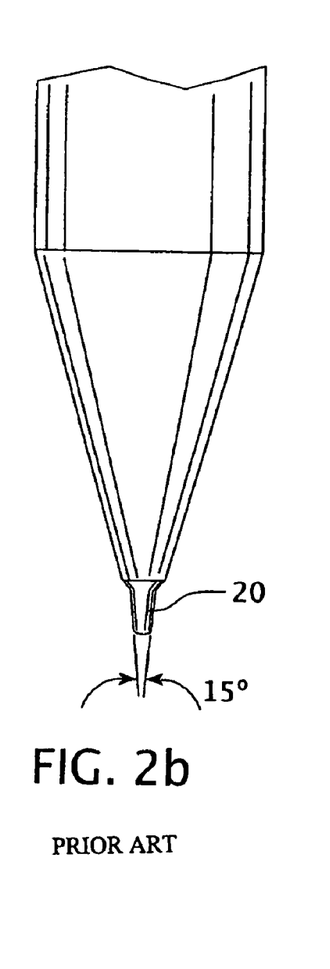
Figure 2C:
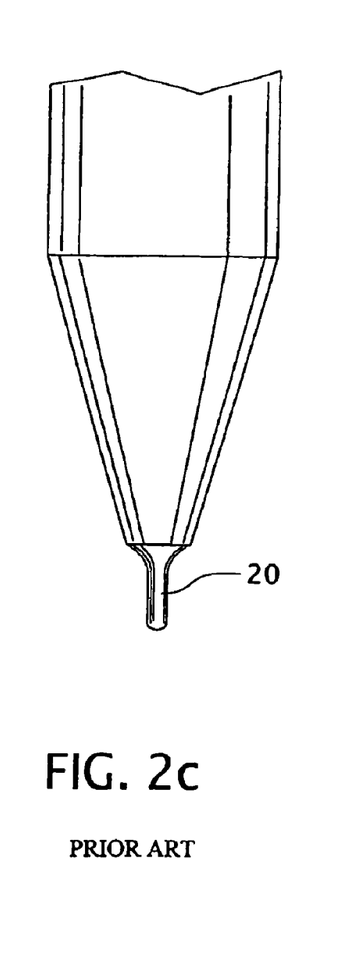
Figure 2D:
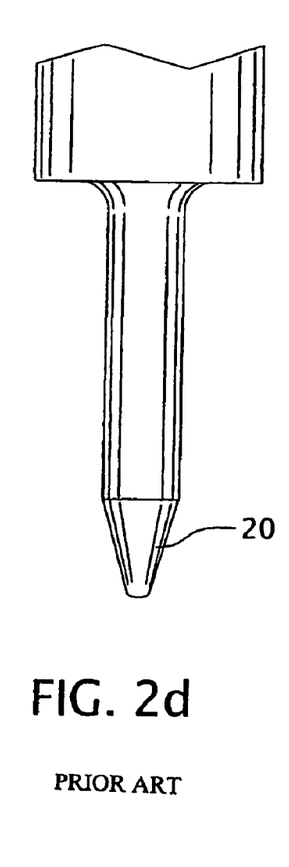
Figure 3:
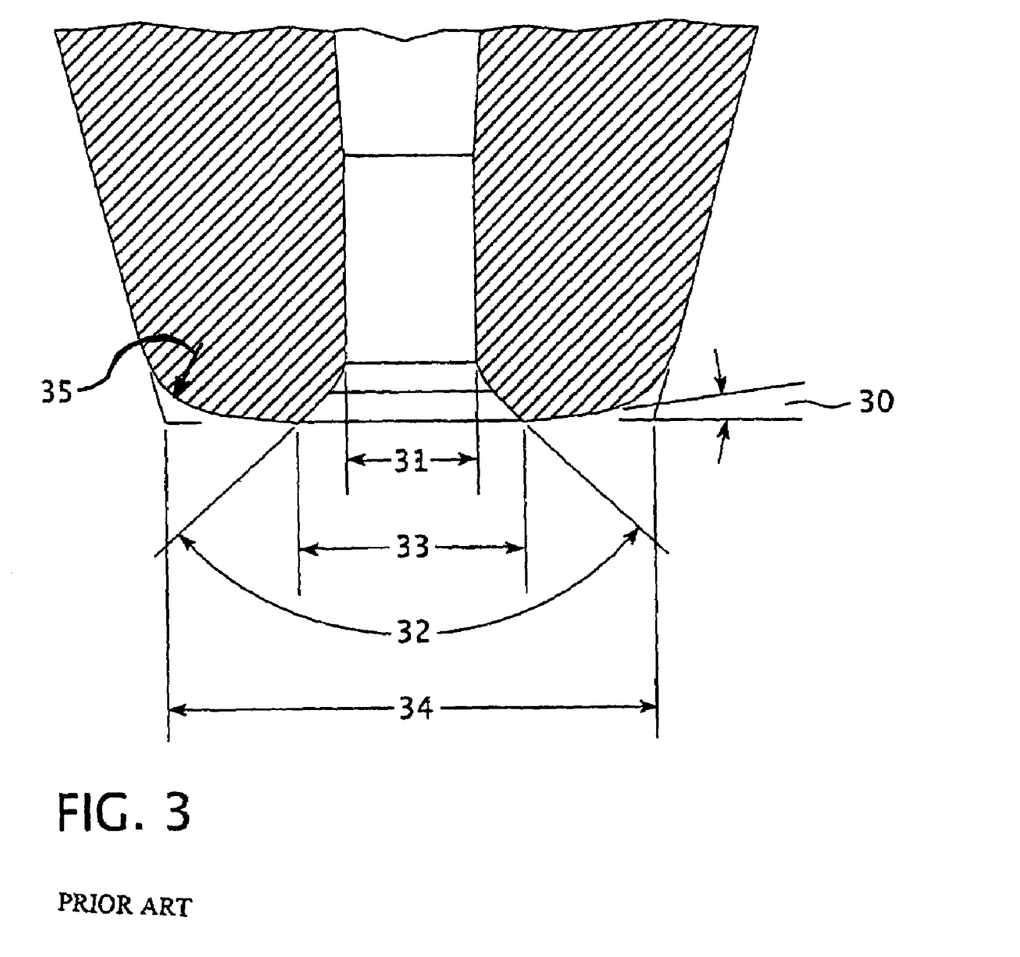

Various views and different versions of commercially available ceramic wire bonding capillary tips are shown in FIGS. 1 through 3. FIG. 1a is a side sectional view of the sample injection tip 10 having an aperture 12 there through which aperture widens to a bell 14. The sample travels through the aperture 12 and the bell 14 to create a "Taylor cone" 16 of electrospray ionized sample downstream of the bell, at the terminus of the sample injection tip, which Taylor cone narrows to a jet 18 of sample which in turn creates a sample plume 20 into the mass spectrometer. All types of electrospray ionized sample tips must create a Taylor cone properly to electrospray the analytes such that once they are devolvated into gas phase ions, they can be steered by the ion optics controlled within the mass spectrometer. Without such a charge, the ions would not be directed by the ion optics for entrance into the mass spectrometer for subsequent detection.

FIG. 1b is a perspective view of the same tip as shown in FIG. 1a, shown in an upright position along line 1b-1b of FIG. 1a, showing the aperture 12 and the bell 14. Except for its blunt nose, bell-terminated aperture and material composition, the sample injection tip is generally similar to other ESI tips known in the art, and it is believed that the shape, dimensions and ceramic material contribute to the new and unexpected features attributable to this sample injection tip.

Surprisingly, it has been found that when the ceramic capillary wire bonding tip is employed having the outer blunt, rather than pointed, terminus, and with an aperture which flares into a bell as shown in FIG. 1a, electrospray ionization is vastly improved compared to the sharply pointed emitters of the prior art. As with all tips of this type, the structure is connected to a sample source via a feed line. It is believed that both the ceramic material and the unique shape, as compared to conventional ESI tips, contribute to avoidance of arcing due to high voltages as well as superior electrospray ionization. As explained above, although conventional teaching is that prior art emitters are sharply pointed to try to increase the electric field by maintaining the same voltage and decreasing the outer diameter of the tip to as small a point as possible, the relatively blunt nosed ceramic capillary sample injection tip easily achieves the necessary high voltages/electric fields.

The ceramic wire bonding capillary tips are commercially available in different sizes. One embodiment of a ceramic capillary sample injection tip used as an ESI tip can be configured with an inner aperture diameter of from about 25 µm to about 38 µm, whereas at the outermost edge of the bell 14 the inner diameter is between 38-68 micrometers and the outer diameter of the sample injection tip at its terminus can be from about 74 µm to about 200 µm. In further embodiments, the sample injection tip can have an aperture with and inner diameter of from about 34±5 µm, a bell shaped void having a maximum inner diameter of about 55±5 µm, and an outer diameter of the terminus of about 135±5 µm. Within these dimensions, the sample injection tip can spray in both nanospray and microspray flow regimes due to the high efficiency promulgated by the ceramic material and the attendant shape and dimensions. The ceramic can be alumina (aluminum oxide) or alumina doped with zirconia or synthetic ruby (alumina doped with chromium oxide). In further embodiments, preferred ceramics can be the aluminum oxides because they are less brittle and thus less breakable than other ceramic materials.

With improved electrospray ionization, mass spectral quality is improved through reduction of the background noise, improvement of the signal/noise ratio and production of the relatively higher charge state ions of the sample. In FIG. 1a, the "Taylor cone" 16 of the sample, which entrains into the jet 18 and thence into the plume 20, can be visualized and, in side sectional view, the counterintuitive design of the aperture 12 and the bell 14 to generate such a Taylor cone, jet and plume, is readily apparent.

Figure 4:
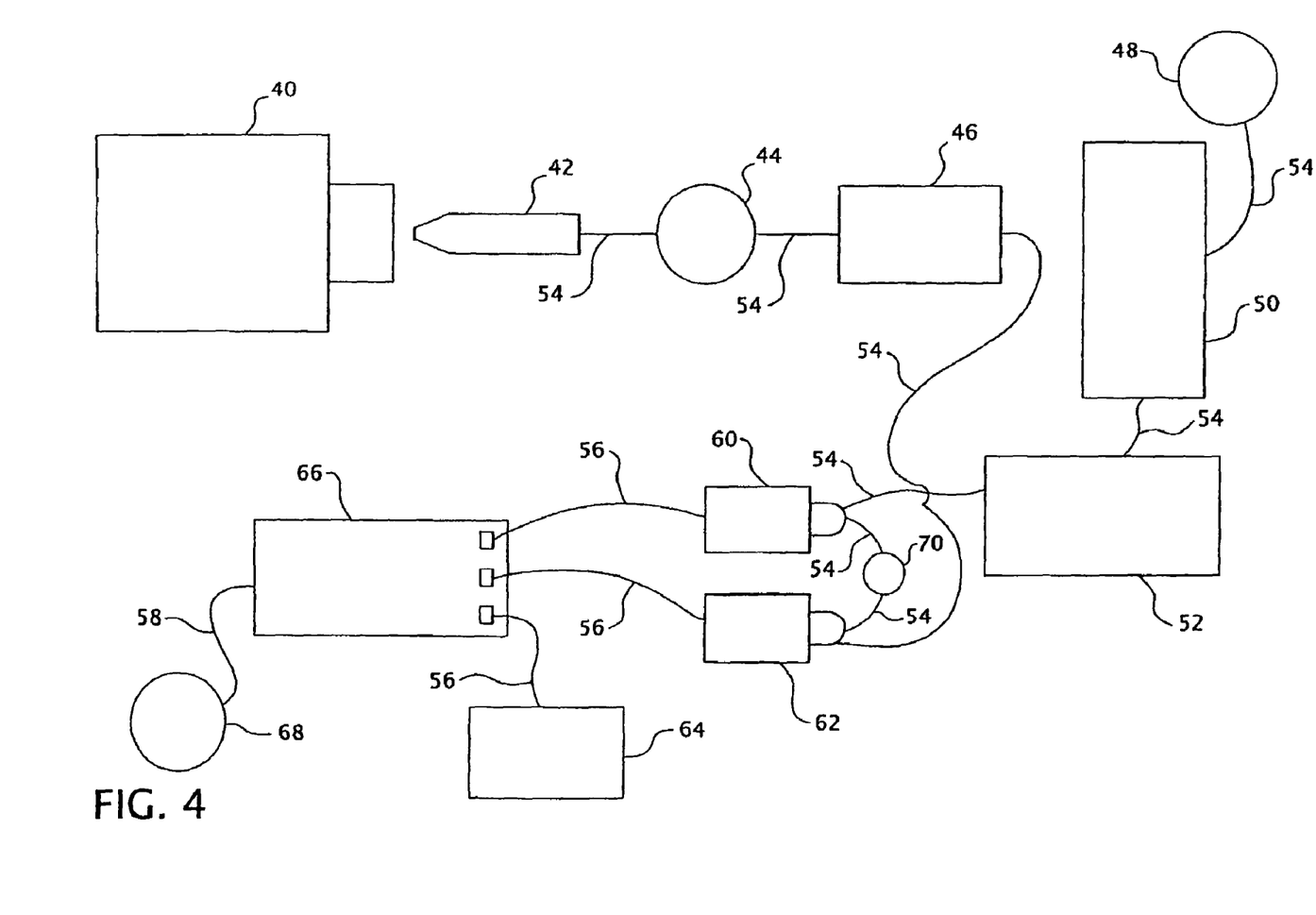
FIG. 4 is a schematic view of an embodiment of the add-on device, of which the mass spectrometer 40 forms no part thereof.
Figure 5:
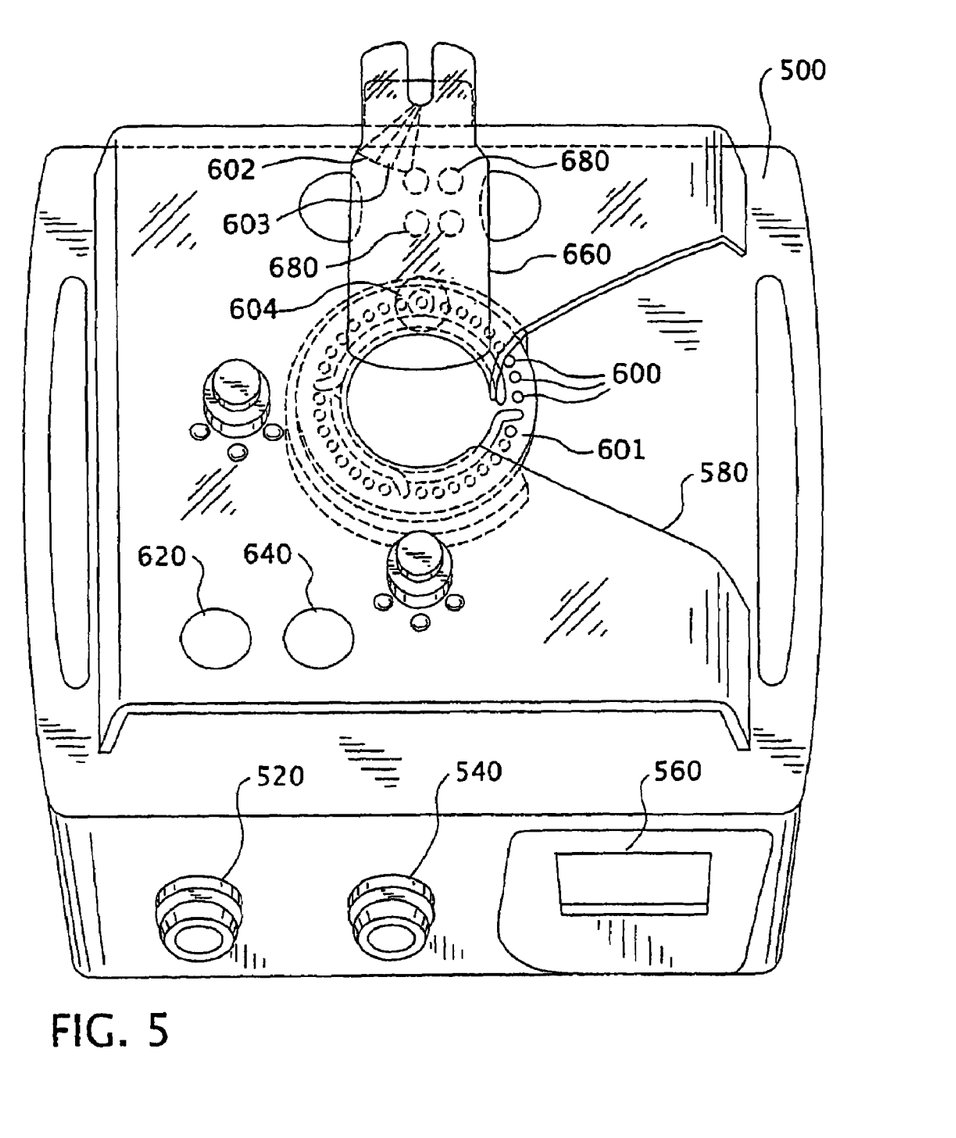
FIG. 5 is a perspective view of an embodiment of the add-on device.

It is also to be understood that the sample injection tip as described herein may be used in other applications involving electrospray ionization in addition to mass spectrometry. The sample injection tips are appropriate anywhere a tiny sample of any material needs to be introduced, via electrospray ionization, into another environment, presumably but not necessarily for analysis. Sample injection for other types of spectroscopy are contemplated, and industrial or medical sample transfers, including patient treatments are, without limitation, also contemplated within the scope of the invention. Having said that, in the mass spectrometry context, users can conservatively expect up to a 50% improvement in signal when using the present ceramic capillary sample injection tip as contrasted with ESI emitters known in the art.

FIGS. 2*a*, 2*b*, 2*c* and 2*d* illustrate alternative sample injection tip shapes, shown in side sectional view, that are commercially available. All of these alternative shapes are typified by the blunt terminus to the sample injector tip 20, as compared to the more sharply pointed tips of the prior art. Sample dimensions and Taylor cone angles are marked.

Finally, and referring once again to FIG. 1*a*, it should be understood that the aperture 12 may transition to the bell 14 with more or less taper than is shown in FIG. 1*a*. The degree of the taper is less important than the aperture and bell diameters. Interestingly, although for many inventions sizes are not particularly relevant, because of the nature of the sample injection tip and the molecular and ionic realities of the samples, dimensions are relevant to the use of the ceramic capillary sample injection tip.

Referring now to FIG. 3, which shows a side sectional view of the same tip as shown in FIG. 1*a* except for its vertical orientation, certain values for various features of a ceramic capillary sample injection tip for an electrospray ionization process can include the following: the Face Angle 30 may range from about 0 to about 11 degrees; the aperture diameter 31 may range from about 5 μm to about 178 μm; and the chamfer diameter (or maximum bell diameter) 33 may range from about 35 μm to about 254 μm. The chamfer angle (bell angle) 32 may range from about 90 degrees to about 120 degrees; the outer diameter (tip terminus) 34 may range from about 38 μm to about 360 μm, and the outer radius 35, that is, the outer radius of the sample injection tip upstream of the terminus, can have a generally unlimited size.

Referring now to FIG. 4, a mass spectrometer 40 (not part of the present add-on device) is positioned immediately adjacent the sample injection tip 42, with all cooperating mass spectrometer/tip adjunct equipment being known in the art. The sample injection tip 42 can be connected, via one of many feed lines 54, to a C8 or C18 "capillary column" (nano) 44. The capillary column 44 can be connected, via a feed line 54, to a high voltage source 46. Upstream, a syringe 48 allows material injection via a feed line 54 to an optional gel electroelutor 50, which can in turn be connected via a feed line to a separator device utilizing tangential fluid flow 52, which can be connected in turn to a first switching valve 60. Feed lines 54 can interconnect the separator device 50 as shown, in combination (optimally) with a second switching valve 62 and an optional trap column (micro) 70. The switching valves can be governed by a computer 68, such as a personal computer, via add-on device electronics 66, in turn connected to the switching valves 60 and 62 and an optional control panel 64, such as an LCD touch screen, via electronic connections 56. The switching valves 60, 62 can typically be double pull, double throw type switching valves, of which the valves in U.S. Pat. No. 6,942,793 are representative. An embodiment of the add-on device can include one each of a six port and a ten port switching valve. The individual switching valves, electronics and electronic connections, and feed lines of FIG. 4 are all well known in the art, and a single pole, single throw two-position six port switching valve is conventionally used in connections adjacent mass spectrometers.

Many of the structures of the add-on device, such as a sample tray for storing tubes such as PCR tubes, are optimally all combined on a single tray type (platform) device that can be carried to and from the add-on unit by each individual user. Indeed, individual users may take advantage of a multiple of separate platforms and/or ESI assembly mounts for a variety of different projects, both for convenience and for avoidance of sample cross-contamination between projects. The add-on unit itself may be carried to and from the mass spectrometer. How the various structures described individually herein can be combined and sub-combined will be readily apparent from the drawing figures.

Referring now to FIG. 5, the basics of the juxtaposition of the inventive add-on unit, a removable platform and a removable ESI assembly mount, as discussed in the previous paragraph, are shown in perspective view. The combination of the add-on unit, the platform and the ESI assembly mount yield a flexible and universal system that adapts to any user's laboratory routine and multiple chromatographic options in any permutation. FIG. 5 is for spatial illustrative purposes only, because the various combinations and potentially customized connections of the present add-on unit, whether facilitated with a portable platform or not, are readily apparent from FIG. 4. As depicted, the add-on unit 500 having a first switching valve 520 and a second switching valve 540 adjacent a touch screen 560. A snap-on platform 580 can be positioned over multiple sample storage tube receptacles 600 in a rotating annular sample tray 601 accessible in the add-on unit itself, under the platform 580. Gel electroelutor bracket 620 and tangential flow separator bracket 640 are simple apertures in the platform 580 and are designed to assist the spatial positioning of the gel electroelutor and separator device with tangential fluid flow when either or both are placed in their respective aperture brackets. Any other configuration of bracket may be substituted. The ESI assembly mount 660 with its feet 680 sit atop and/or through corresponding apertures in the platform 580 to provide a stable surface new the multiple sample storage tube receptacles 600, to hold the structures of the ESI assembly including the triangular sample injection tip cartridge mount 602, the sample injection tip cartridge 603, the high voltage source (not shown) and the fraction collector inlet 604. The triangular sample injection tip cartridge mount 602, the sample injection tip cartridge 603, the high voltage source (not shown) and the fraction collector inlet 604 are all borne atop the platform 580 and underneath the top surface of the ESI assembly mount 660. The connecting feed lines and electronic connections, and electronics and computer connection (ethernet) are likewise not shown in this perspective view, and are well within the skill of the art for multiple permutations of all the possible components. Any number of additional chromatography columns or devices may be added to create any custom sample separation or preparation step. Generally, all the feed lines and connections are provided in semi-permanent or permanent attachment to the add-on unit 500, so that the platform 580 may be detached at will from all the feed lines and connections and a different platform substituted therefore at any time. Commercially available PCR tubes, such as strips of banded PCR tubes customarily banded in rows of eight, may be placed in the sample storage tube receptacles 600 for filling as the sample tray 601 rotates as controlled by a motor and software, to eject a fraction of sample through the fraction collector inlet 604 and concomitantly into a sample storage tube (not shown).

Gel Electroelution Device

The gel electroelutor of the present invention was designed to extract, reproducibly and efficiently, electrophoretically separated intact proteins from SDS-PAGE (sodium dodecyl sulfate polyacrylamide gel electrophoresis) gel matrix. The design of the gel electroelutor incorporates the combination of electroelution and hydrodynamic flow to permit the successful, reproducible extraction of gel-separated proteins. Following electrophoretic separation of proteins on an SDS-PAGE gel, the proteins are visualized using a non-fixing stain (i.e., modified Coomassie or SYPRO orange stain). The protein bands are excised from the gel using a tubular spot picker, which is then inserted into a gel spot well in the gel electroelutor body. The gel electroelutor then uses a low applied voltage and flow through buffer to establish an electric field across the gel spot. The protein band electrophoretically migrates out of the gel and into the flow through buffer, which carries the extracted proteins out of the gel electroelutor for collection in a reservoir or solid phase extraction trapping column, for example a C8 solid phase extraction trapping column. Alternatively, the collected proteins, and buffer solution, can be transferred to a separator device, as described below, for further processing. The specific gel electroelutor body design, incorporating the electrodes for establishment of the cross-gel electric field and the channels for hydrodynamic pumping of flow through buffer, permit efficient and reproducible extraction of intact proteins from SDS-PAGE gels.

Figure 6:
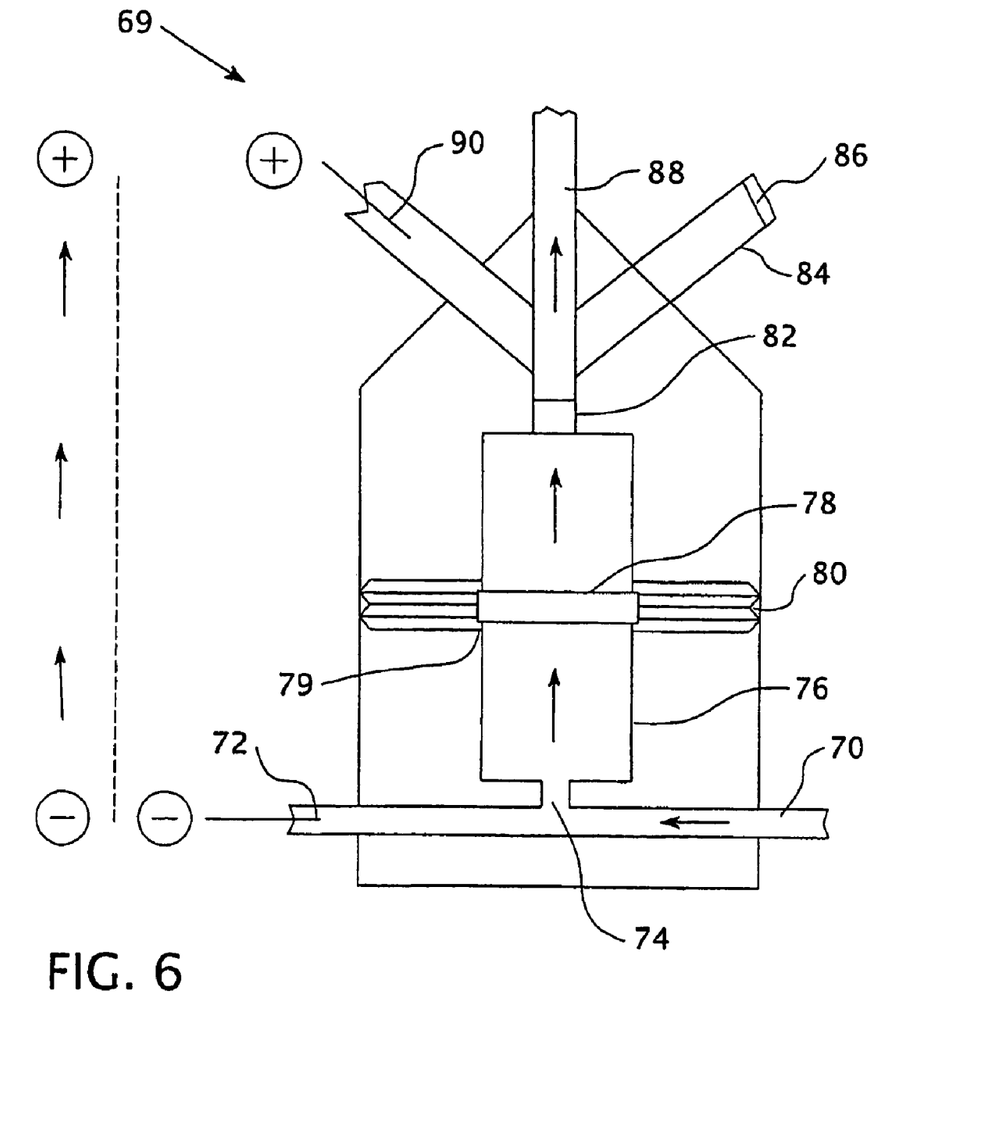
FIG. 6 is a side sectional view of an embodiment of a gel electroelution device.

Referring now to FIG. 6, the gel electroelutor 69 of the present invention is illustrated in side sectional view. An embodiment of the gel electroelution device can generally comprise a gel spot column, a gel well within the gel spot column, wherein the gel well receive a gel spot having a size (e.g., diameter) equal to the size (e.g., diameter) of the gel spot column, such that no gap exists between the gel spot and the side walls. The gel electroelution device can further comprise an inlet and an outlet, each in selective fluid communication with the gel spot column, a frit plug intermediate the gel spot well and the outlet; a positive electrode in fluid communication with said inlet, and a negative electrode in fluid communication with the outlet, such that an electric field is created in the same direction as the fluid flow. A purge line can also be provided in selective fluid communication with the gel spot column intermediate the gel well and the outlet.

As described previously, a gel spot is cut with a tubular spot picker (similar to using a plastic straw to cut gelatin) and the gel spot 78 is placed within a gel spot well 79, in the gel spot column 76 of the gel electroelutor 69. Upstream of the gel spot 78 is the inlet 70; adjacent the inlet 70 is a sealed negative electrode 72. Fluid, typically buffer without additional sample components, travels from the inlet 70 to the gel spot column inlet 74 and from thence through the gel spot 78 to and through the frit plug 82. The frit plug prevents micron sized particles of gel from traveling downstream as foulants. Frit plugs are well known in the art, and are commercially available from a number of suppliers. Downstream of the frit plug 82 is a purge line 84 (for removing air bubbles, for example) that terminates in a purge line plug 86. Adjacent the purge line 84 is a sealed positive electrode 90. The electric field thus forms in the same direction to the fluid flow, and the protein band already having been determined to be of interest thus electrophoretically migrates out of the gel and into the flow through buffer, which carries the extracted proteins through the frit plug and further downstream to any desired further separation or preparation unit via the outlet 88. It should be noted that prior art static tubes for gel spot electroelution never enjoyed the continuous flow advantage the present gel electroelutor affords. Also, with the gel spot 78 having a diameter which leaves no gap between the gel spot 78 and the gel spot well 79 (which is shown as an annular recess in the wall of the gel spot column 76), separations are enhanced as contrasted with prior art gel eluting tubes that allowed space between the gel and the tube wall and concomitant co-admixing of upstream and downstream flows. Additionally, a sweep line can be configured to the purge line port 84 to provide additional flow for removal of any protein sample remaining within the gel electroelutor outlet line.

Separator Device

Downstream of the optional gel electroelutor described above is the also optional separator device, which can utilize tangential fluid flow. The separator device was developed to assist researchers in the concentration, purification, and preparation of protein samples for analysis. The separator device can employ a molecular weight cut-off filter (MWCO)

or dialysis membrane that effectively acts as a sieve for biological sample solutions. Analytes and solvent molecules whose size is below the MWCO (pore size) pass through the membrane as the filtrate, while sample molecules whose size is above the MWCO are retained in the reservoir above the membrane as the retentate. Variable plumbing connections utilizing a standard switching valve permit collection of either the retentate or the filtrate for subsequent analysis. Inside the separator device with tangential fluid flow, the retentate can be rinsed, desalted, purified and concentrated. Additionally, the retentate reservoir can be used as a reaction chamber for fluorescent labeling of proteins and for reduction/alkylation of proteins prior to enzymatic digestion. Using an appropriate reagent, the separator device with tangential fluid flow can be used to remove SDS detergent from proteins trapped in the retentate reservoir.

Figure 7A:
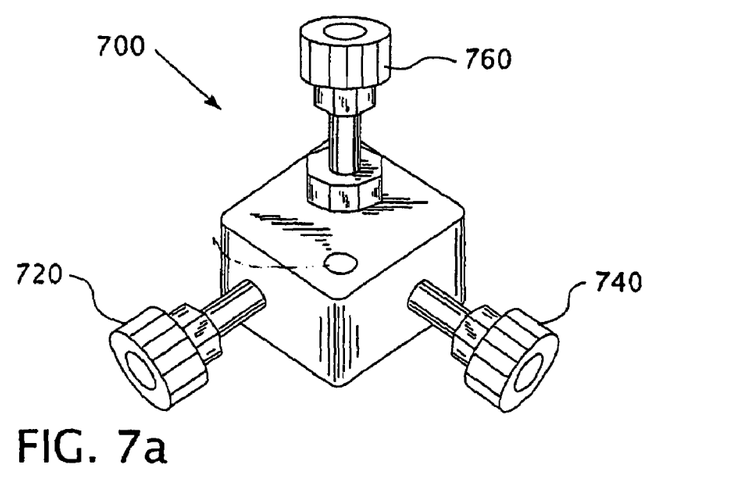
FIG. 7a is a perspective view of an embodiment of a separator device with tangential fluid flow.
Figure 7B:
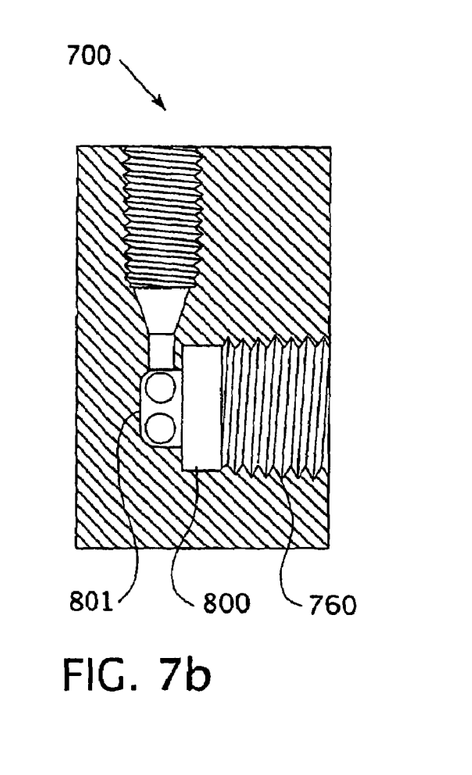
Figure 7C:
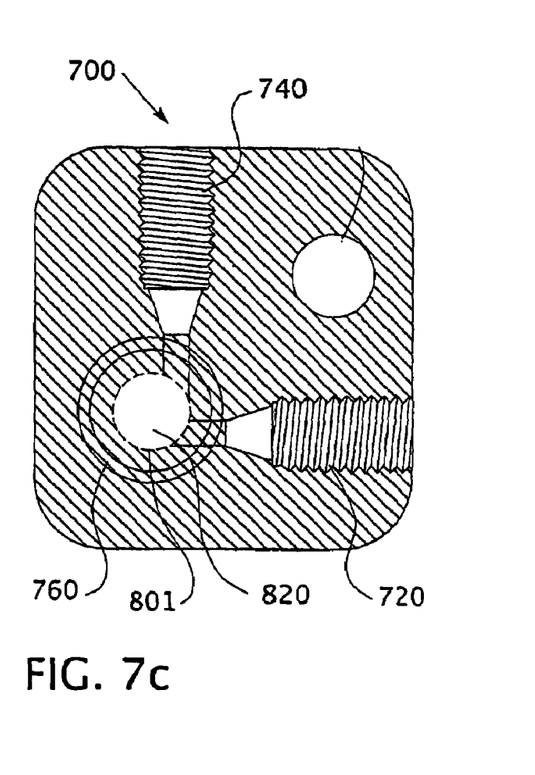

Referring now to FIGS. 7a through 7c, an embodiment of the separator device 700 can generally comprise an inlet port 720, retentate port 740 and filtrate port 760, which are each in selectively controlled fluid communication with a chamber well, or central well 810. The MWCO or dialysis membrane (filter) can be provided intermediate the inlet port 720 and the filtrate port 760. The central well 801 can be generally cylindrical, and each of the inlet port 720 and retentate port 740 can intersect the central well 801 in a generally tangential orientation such that a cyclonic flow is induced in the central well 801. The three ports of the separator device 700 may be color coded to signify inlet, filtrate and retentate, but the inlet port 720, the retentate port 740 and the filtrate port 760 are so numbered.

Referring particularly to FIGS. 7b and 7c, horizontal and vertical sectional views of the separator device 700 show that a shoulder 800 where the MWCO or dialysis membrane seals against is positioned adjacent the filtrate port 760, and hence all filtrate has passed through the MWCO (or dialysis membrane) filter. However, it may be seen that the inlet port 720 and the retentate port 740 intersect the cental well 801 in a generally tangential manner, e.g. they connect in an off-center, generally orthogonal orientation into the central well 801 (visible in dotted line in FIG. 7c due to the overlaying filter 820). The pressure of the sample solution entering the central well 801 provides hydrodynamic pressure that pushes bulk solvent and other molecules that are below the MWCO through the pores of the MWCO or dialysis membrane. Proteins and other larger molecules can become lodged in the membrane pores or adsorb to the membrane surface, leading to fouling of the membrane. The off-center, orthogonal orientation of the inlet flow creates a tangential, or sweeping, flow in the central well 801 that can prevent proteins from experiencing a static downward pressure at the membrane surface, thus reducing clogging events in the pores. Additionally, the tangential flow design improves flushing out of the chamber during retentate collection. The geometry of the inlet port 720 and the retentate port 740 essentially induces a cyclonic flow during retentate collection, similar to the cyclonic flow when a commode is flushed. The cyclonic action produces a high tangential flow that helps to sweep adsorbed and lodged proteins from the membrane surface, thus improving protein sample recovery. The filter 820 is any MWCO filter or dialysis membrane as within the skill of the art. Typical filters of this type are paper discs with a polymer coating, such as a multi-layer polymer coating, or dialysis membranes fabricated from regenerated cellulose or other polymers known in the art, in the side of the filter facing the central well 801. Pore size and compatibility features for such MWCO filters and dialysis membranes are well known, and filters of this type are available, for example, from Pall Corporation, Ann Arbor, Mich. or Spectrum Laboratories, Rancho Dominguez, Calif.

Prior to the present innovations, any functionalities similar to the present gel electroelution device and/or separator device were performed off-line. Consequently, an embodiment of the add-on device having these sample preparation components is therefore more than a mere automation of previously disparate operations: use of these two devices in an in-line fashion benefits enormously from a continuous flow system and the efficiency which continuous wet processing affords, as contrasted with largely dry separations in centrifuges known in the prior art.

Figure 8:
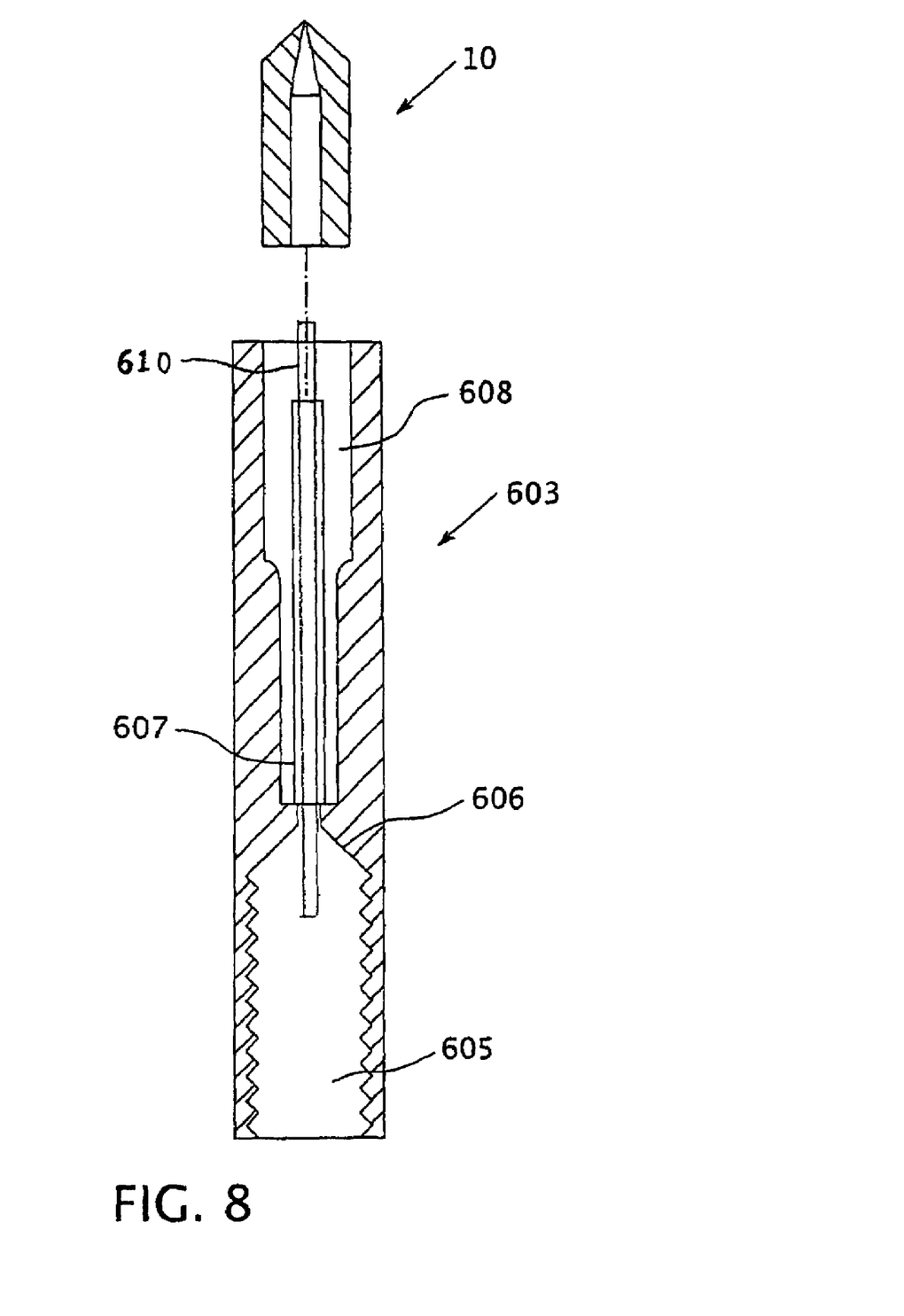
FIG. 8 is a sectional view of an embodiment of a sample injection tip cartridge.

The ceramic capillary wire bonding sample injection tip 10 may be combined with a sample injection tip cartridge 603, and a sample injection tip cartridge mount 602 (not shown), as further illustrated in FIG. 8.

Sample Injection Tip Cartridge

FIG. 8 is a sectional view of an embodiment of a sample injection tip cartridge 603 with a threaded aperture 605, a center inlet 606, a center inlet tube 607, and a sample injection tip receptacle 608. Also, in this way the sample injection tip cartridge 603 may be borne in or on the sample injection tip cartridge mount 602, as shown in FIG. 5. The cartridge can be mounted so as to be able to rotate in at least one plane, for example, laterally, in order to permit adjustment of the angle of the sample injection tip 10, for example 0, 25 or 50 degrees, relative to the mass spectrometer entrance (such lateral angle being measured from a "z" axis straight into the entrance of the spectrometer). The cartridge can also act as a fluid coupling, providing a sealed connection between the aperture in the sample injection tip and the source of the fluid sample. In this way the sample tip can be quickly and easily removed and replaced with other sample tips without having each time to also reconnect the tip aperture to the tubing from the liquid sample source.

The screen of a governing computer can provide for 8 bullets (e.g., buttons or links), for example, one each for "electroelution," "fraction," "collection," "digestion," "separation" and "analysis." Each of these links permits governance and upload of the associated software (and motor control and etc.) to support each of the eight functions so identified. The add-on device thus embraces not only the above-described add on unit but also the method of governing the unit with eight key commands and upload functions.

Although the invention has been described with particularity above, with reference to particular structures, materials and methods, the invention is to be limited only insofar as is set forth in the accompanying claims.

What is claimed is:

1. An electrospray ionization process comprising flowing a liquid through a capillary wire bonding tip and applying sufficient voltage to electrospray said liquid sample as it is discharged from said capillary wire bonding tip.

2. The electrospray ionization process of claim 1 wherein said capillary wire bonding tip is made of a ceramic comprised of aluminum oxides.

3. The electrospray ionization process of claim 2 wherein said capillary wire bonding tip is made of a ceramic comprising one of alumina doped with chromium oxide and alumina doped with zirconia.

4. The electrospray ionization process of claim 1 further comprising hydrodynamically passing said liquid sample through said capillary wire bonding tip.

5. An electrospray ionization process comprising:
   a. passing a liquid sample through an axially disposed aperture in a sample injection tip, wherein said aperture has a diameter of from about 5 μm to about 178 μm, and said sample injection tip has a terminus with an outer diameter of from about 25 μm to about 360 μm; and
   b. applying sufficient voltage to electrospray said liquid sample as it is emitted from said sample injection tip.

6. The electrospray ionization process of claim 5 wherein said aperture terminates in a bell-shape.

7. The electrospray ionization process of claim 6 wherein a chamfer is provided intermediate said bell-shape and said terminus.

8. The electrospray ionization process of claim 7 wherein said chamfer has a diameter of from about 35 μm to about 254 μm.

9. The electrospray ionization process of claim 8 wherein said chamfer has a diameter of from about 38 μm to about 68 μm.

10. The electrospray ionization process of claim 5 wherein said aperture diameter is from about 25 μm to about 39 μm.

11. The electrospray ionization process of claim 5 wherein chamfer diameter is from about 50 μm to about 55 μm.

12. The electrospray ionization process of claim 5 wherein said outer diameter of said terminus is from about 129 μm to about 140 μm.

13. The electrospray ionization process of claim 5 wherein said sample injection tip is made of a ceramic comprised of aluminum oxides.

14. The electrospray ionization process of claim 13 wherein said sample injection tip is made of a ceramic comprising one of alumina doped with chromium oxide and alumina doped with zirconia.

15. The electrospray ionization process of claim 5 wherein said sample injection tip is a ceramic capillary wire bonding tip.

16. The electrospray ionization process of claim 5 further comprising hydrodynamically passing the liquid sample through the aperture.

17. An add-on device having a sample injection tip for electrospray ionization of a liquid sample passed through said sample injection tip, wherein said sample injection tip comprises a capillary wire bonding tip.

18. The add-on device of claim 17 wherein said capillary wire bonding tip is made of a ceramic comprised of aluminum oxides.

19. The add-on device of claim 18 wherein said capillary wire bonding tip is made of a ceramic comprising one of alumina doped with chromium oxide and alumina doped with zirconia.

20. The add-on device of claim 17 wherein said liquid sample is hydrodynamically pumped through said capillary wire bonding tip.

21. An add-on device having a sample injection tip for electrospray ionization of a liquid sample passed through said sample injection tip, wherein said sample injection tip comprises:
   a. an axially disposed aperture having a diameter of from about 5 μm to about 178 μm; and
   b. a terminus having an outer diameter of from about 25 μm to about 360 μm.

22. The add-on device of claim 21 wherein said aperture terminates in a bell-shape.

23. The add-on device of claim 22 wherein said sample injection tip further comprises chamfer intermediate said bell-shape and said terminus.

24. The add-on device of claim 23 wherein said chamfer has a diameter of from about 35 μm to about 254 μm.

25. The add-on device of claim 24 wherein said chamfer has a diameter of from about 38 μm to about 68 μm.

26. The add-on device of claim 21 wherein said aperture diameter is from about 25 μm to about 39 μm.

27. The add-on device of claim 21 wherein chamfer diameter is from about 50 μm to about 55 μm.

28. The add-on device of claim 21 wherein said outer diameter of said terminus is from about 129 μm to about 140 μm.

29. The add-on device of claim 21 wherein said sample injection tip is made of a ceramic comprised of aluminum oxides.

30. The add-on device of claim 29 wherein said sample injection tip is made of a ceramic comprising one of alumina doped with chromium oxide and alumina doped with zirconia.

31. The add-on device of claim 21 wherein said sample injection tip is a ceramic capillary wire bonding tip.

32. The add-on device of claim 21 further comprising aid sample injection tip in selective fluid communication with at least one of a gel electroelution device and a separation device.

33. The add-on device of claim 32 wherein both said gel electroelution device and said separation device are in selective fluid communication with and upstream of said sample injection tip.

34. The add-on device of claim 32 wherein said gel electroelution device comprises:
   a. a gel spot column;
   b. a gel well within said gel spot column, said gel well defined by one or more side walls, said gel well adapted to receive a gel spot having a size which permits no gap between said gel spot and said one or more side walls;
   c. an inlet and an outlet, each in selective fluid communication with said gel spot column;
   d. a frit plug intermediate said gel spot well and said outlet; and
   e. a positive electrode in fluid communication with said inlet and a negative electrode in fluid communication with said outlet, such that an electric field is created in the same direction as the fluid flow.

35. The add-on device of claim 34 wherein said gel electroelution device further comprises a purge line in selective fluid communication with said gel spot column intermediate said gel well and said outlet.

36. The add-on device of claim 32 wherein said separator device comprises:
   a. a central well in selective fluid communication with an inlet port, a filtrate port, and a retentate port; and
   b. a filter intermediate said inlet port and said filtrate port.

37. The add-on device of claim 36 wherein said central well is generally cylindrical, and each of said inlet port and retentate port intersect said central well in a generally tangential orientation such that a cyclonic flow is induced in said central well.

38. The add on device of claim 36 wherein said inlet, retentate and filtrate ports are marked with different colors.

39. The add-on device of claim 32 further comprising a fraction injection inlet in selective fluid communication with at least one of said gel electroelution device, said separator device, and said sample injection tip.

40. The add-on device of claim 39 further comprising a rotating sample tray having a plurality of sample wells, said rotating sample tray mounted adjacent said fraction injection inlet.

41. The add-on device of claim 40 further comprising at least one valve operable to selectively control said selective fluid communication between at least one of said fraction injection inlet, said gel electroelution device, said separator device, and said sample injection tip.

42. An add-on device having a sample injection tip for electrospray ionization of a liquid sample passed through said sample injection tip, said add-on device comprising:
  a. a sample injection tip cartridge connected to said add-on device in a manner to permit rotation thereof in at least one plane; and
  b. said sample injection tip removably supported by said cartridge, such that ionized liquid sample can be discharged from said sample injection tip a direction selectable by rotating said cartridge in said at least one plane.

43. The add-on device of claim 42 wherein said cartridge further comprises a fluid coupling between said sample injection tip and a source of said liquid sample.

* * * * *